US008299280B2

(12) United States Patent
Ramjugernath et al.

(10) Patent No.: US 8,299,280 B2
(45) Date of Patent: Oct. 30, 2012

(54) RECOVERY OF COMPONENTS MAKING UP A LIQUID MIXTURE

(75) Inventors: Deresh Ramjugernath, Durban (ZA);
Paramespri Naidoo, Durban (ZA);
Clinton Shalendra Subramoney, Durban (ZA); Michael Wayne Nelson, Tongaat (ZA)

(73) Assignee: University of Kwazulu-Natal, Durban (ZA)

( * ) Notice: Subject to any disclaimer, the term of this patent is extended or adjusted under 35 U.S.C. 154(b) by 472 days.

(21) Appl. No.: 12/606,254

(22) Filed: Oct. 27, 2009

(65) Prior Publication Data
US 2010/0105932 A1    Apr. 29, 2010

(30) Foreign Application Priority Data
Oct. 27, 2008    (ZA) .................................... 08/9204

(51) Int. Cl.
*C07D 301/32* (2006.01)
*C07C 17/38* (2006.01)
(52) U.S. Cl. .................. 549/541; 570/177; 570/178
(58) Field of Classification Search .............. 549/541; 570/177, 178
See application file for complete search history.

(56) References Cited

U.S. PATENT DOCUMENTS

| 3,326,780 A | 6/1967 | Wiist |
| 3,775,439 A | 11/1973 | Atkins, Jr. |
| 4,134,796 A | 1/1979 | Oda et al. |
| 4,288,376 A | 9/1981 | Ohsaka et al. |
| 4,356,291 A | 10/1982 | Darling |
| 4,358,348 A | 11/1982 | Sulzbach |
| 4,902,810 A | 2/1990 | Ikeda et al. |
| 2005/0027132 A1 | 2/2005 | Takagi et al. |
| 2005/0043422 A1 | 2/2005 | Shibanuma et al. |

FOREIGN PATENT DOCUMENTS

JP    09-020765    1/1997

OTHER PUBLICATIONS

Holderbaum, T. and J. Gmehling, "PSRK: A group contribution equation of state based on UNIFAC." Fluid Phase Equilibria, 1991. 70: p. 251-265.
Hirao, A., K. Sugiyama, and H. Yokoyama, "Precise synthesis and surface structures of architectural per- and semifluorinated polymers with well-defined structures." Progress in Polymer Science, 2007. 32(12): p. 1393-1438.
Huang, Z., Y. Zhang, C. Zhao, J. Qin, H. Li., m. Xue, and Y. Liu, "Direct gas-phase epoxidation of hexafluoropropylene with molecular oxygen using Ag catalyst." Applied Catalysis A: General, 2006. 303(1): p. 18-22.
Bian, J.F., W.R. Lujan, D. Harper-Nixon, H.S. Jeon, and D.H. Weinkauf, "Effect of hexafluoropropylene oxide plasma polymer particle coatings on the rheological properties of boron nitride/poly (dimethylsiloxane) compostes." Journal of Colloid and Interface Science, 2005. 290(2): p. 582-591.

(Continued)

*Primary Examiner* — Taylor Victor Oh
(74) *Attorney, Agent, or Firm* — Allen, Dyer, Doppelt Milbrath & Gilchrist, P.A.

(57) ABSTRACT

A process for recovering hexafluoropropylene and hexafluoropropylene oxide from a liquid mixture of these components is provided. The process includes, in a stripping stage, contacting the mixture with a gaseous stripping agent, thereby to strip hexafluoropropylene from the mixture. A gaseous product comprising hexafluoropropylene and gaseous stripping agent is withdrawn from the stripping stage, as is a liquid product comprising hexafluoropropylene oxide.

14 Claims, 2 Drawing Sheets

OTHER PUBLICATIONS

Stolarska, M., L. Niedzicki, R. Borkowska, A. Zalewska, and W. Wieczorek, "Structure, transport properties and interfacial stability of PVdF/HFP electrolytes containing modified inorganic filler." Electrochimica Acta, 2007. 53(4): p. 1512-1517.

Aravindan, V. and P. Vickraman, "Polyvinylidenefluoride-hexafluoropropylene based nanocomposite polymer electrolytes (NCPE) complexed with LiPF3(CF3CF2)3." European Polymer Journal, 2007.

Krespan, C.G., "Fluoroalkyl Azide Chemistry." J. Org Chem., 1986. 51(1): p. 332-337.

RECOVERY OF COMPONENTS MAKING UP A LIQUID MIXTURE

FIELD OF THE INVENTION

This invention relates to the recovery of components making up a liquid mixture. More particularly, the invention relates to a process for recovering hexafluoropropylene and hexafluoropropylene oxide from a liquid mixture of these components.

BACKGROUND OF THE INVENTION

Hexafluoropropylene oxide (HFPO) is typically produced from oxidation or epoxidation of hexafluoropropylene (HFP). During such oxidation or epoxidation, only partial conversion of the HFP into HFPO takes place, and the resultant product consequently comprises a mixture of desired HFPO and unreacted undesired HFP. In order to exploit the higher valued HFPO and to recycle the unreacted HFP, it is thus necessary to recover a high purity HFPO product and a high purity HFP product. This is difficult, since HFPO is chemically similar to HFP, and has similar physical properties, e.g. it has a similar boiling point.

SUMMARY OF THE INVENTION

In accordance with the invention, there is provided a process for recovering hexafluoropropylene and hexafluoropropylene oxide from a liquid mixture of these components, the process including:

in a stripping stage, contacting the mixture with a gaseous stripping agent, thereby to strip hexafluoropropylene from the mixture;

withdrawing a gaseous product comprising hexafluoropropylene and gaseous stripping agent from the stripping stage; and withdrawing a liquid product comprising hexafluoropropylene oxide from the stripping stage.

In one embodiment of the invention, the gaseous stripping agent may be carbon dioxide. However, in another embodiment of the invention, the gaseous stripping agent may be hexafluoroethane.

In the stripping stage, the contacting of the mixture with the gaseous stripping agent may be carried out in a packed stripping column. Preferably, the mixture may be contacted with the gaseous stripping agent in counter-current fashion. The gaseous product may thus also contain some entrained hexafluoropropylene oxide. Similarly, the liquid product may thus contain some absorbed stripping agent.

The process may include purifying the gaseous product. The purification of the gaseous product may include recovering, as separate components, hexafluoropropylene, stripping agent and, in some cases, entrained hexafluoropropylene oxide from the gaseous product.

More particularly, the purification of the gaseous product may include distilling it in at least one downstream gaseous product distillation stage. In the distillation stage, stripping agent may be recovered as a distillate, while the hexafluoropropylene and hexafluoropropylene oxide are recovered as a bottoms product. Thus, the process may also include withdrawing a distillate and a bottoms product from the gaseous product distillation stage.

When the gaseous product is purified in the downstream gaseous product distillation stage and a mixture containing hexafluoropropylene and hexafluoropropylene oxide is withdrawn as a bottoms product of the gaseous product distillation stage, the process may include recovering hexafluoropropylene and hexafluoropropylene oxide from the bottoms product of the downstream gaseous product distillation stage by:

in a secondary stripping stage, contacting the bottoms product with a gaseous stripping agent, thereby to strip hexafluoropropylene from the bottoms product;

withdrawing a secondary gaseous product comprising hexafluoropropylene and gaseous stripping agent from the secondary stripping stage;

purifying the secondary gaseous product by distilling it in a secondary downstream gaseous product distillation stage; and withdrawing a secondary liquid product comprising hexafluoropropylene oxide from the secondary stripping stage.

Thus, the bottoms product of the gaseous product distillation stage may be contacted with a gaseous stripping agent in the secondary or downstream bottoms product stripping stage, and the secondary hexafluoropropylene and stripping agent rich gaseous product may be withdrawn from the secondary or downstream bottoms product stripping stage. Likewise, a secondary hexafluoropropylene oxide rich liquid product may be withdrawn from the secondary or downstream bottoms product stripping stage.

The process may include recovering, from the liquid product from the initial stripping stage, hexafluoropropylene oxide in one or more hexafluoropropylene oxide recovery stages. The recovery of the hexafluoropropylene oxide from the liquid product may include distilling the liquid product in a downstream liquid product distillation stage, withdrawing a bottoms product comprising hexafluoropropylene oxide from the liquid product distillation stage, and a withdrawing distillate comprising stripping agent from the liquid product distillation stage.

If desired, purification of the gaseous product may be extended downstream from the bottoms product stripping stage to include secondary or further gaseous product distillation stages and corresponding secondary or bottoms product stripping stages as hereinbefore described. The process may then include withdrawing hexafluoropropylene oxide rich liquid product and hexafluoropropylene and stripping agent rich gaseous product from each stripping stage as well as withdrawing stripping agent distillate and hexafluoropropylene rich bottoms product from each distillation stage. Typically, a multistage stripping process may thus be employed. Therefore, the process may include a plurality of the secondary stripping stages each comprising a secondary gaseous product distillation stage and a secondary downstream liquid product distillation stage with the bottoms product from the downstream gaseous product distillation stage of an upstream secondary stripping stage passing into the next or downstream stripping stage. The process may then further include withdrawing a hexafluoropropylene oxide rich liquid product and a hexafluoropropylene and stripping agent rich gaseous product from each secondary stripping stage with the gaseous product passing into the secondary gaseous product distillation stage of that stripping stage and with the liquid product passing into the secondary liquid product distillation stage of that stripping stage.

The bottoms products from the respective secondary liquid product distillation stages may be combined to form a composite bottoms product stream, i.e. the bottoms products are each individually purified in a distillation stage. Instead, when a multistage stripping process is used, the process may include combining a hexafluoropropylene oxide rich liquid product of each secondary stripping stage so that the combined liquid product can be treated in a single liquid product distillation stage.

The process may include recycling stripping agent which has been recovered from at least one of the gaseous product distillation stages and/or from at least one of the liquid product distillation stages to at least one of the stripping stages. The process may also include purging stripping agent from the process as a stripping agent purge stream, to prevent accumulation of stripping agent in the process.

BRIEF DESCRIPTION OF THE DRAWINGS

The invention will now be described by way of non-limiting example, with reference to the following schematic drawings.

DETAILED DESCRIPTION OF THE PREFERRED EMBODIMENTS

Figure 1:
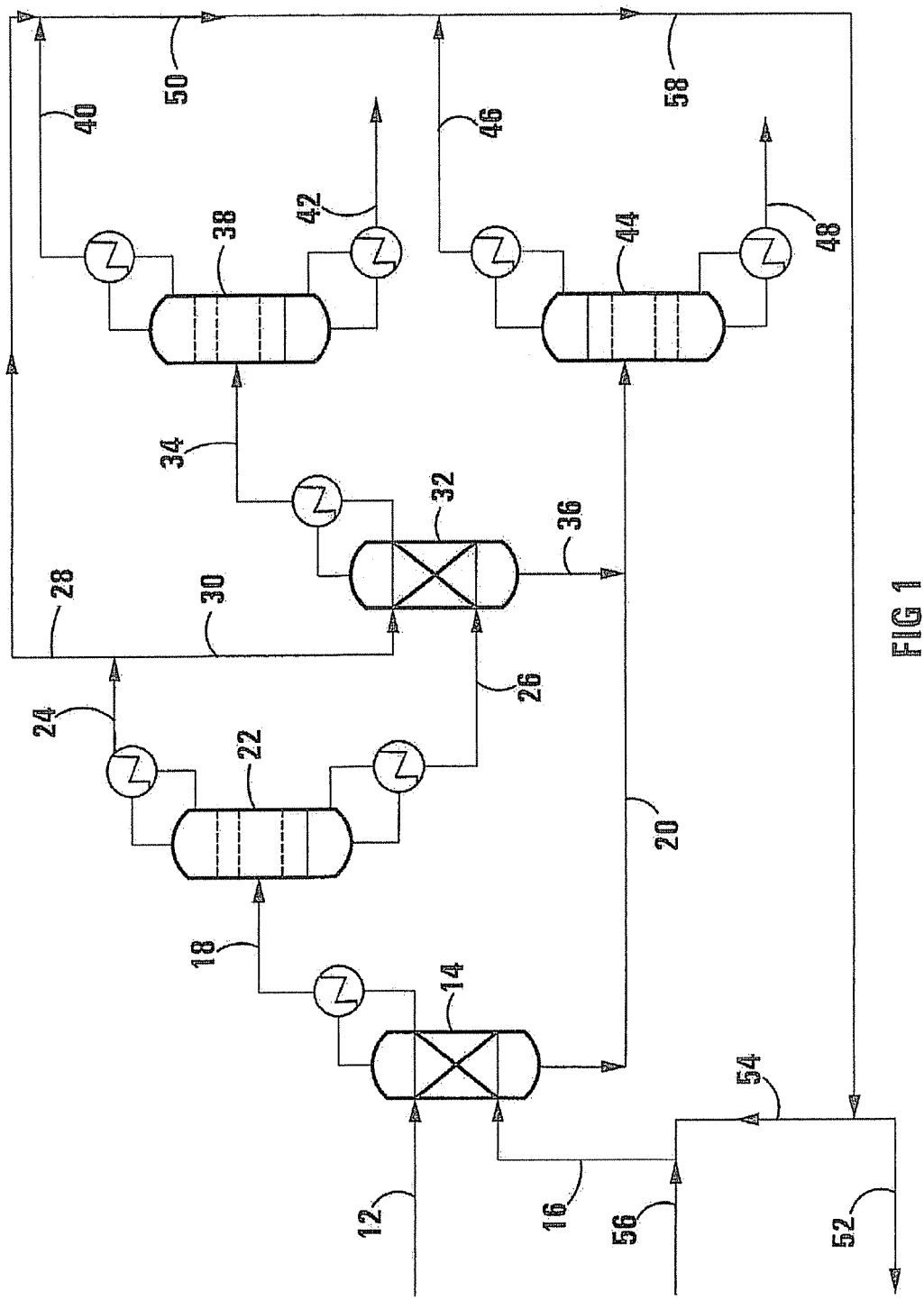
FIG. 1 shows a flow diagram of a process in accordance with a first embodiment of the invention, in which carbon dioxide is employed as a stripping agent.

In the drawings, the same reference numerals are used to indicate the same or similar features.

Referring firstly to FIG. 1, reference numeral 10 generally indicates a process for recovering hexafluoropropylene and hexafluoropropylene oxide from a feed stream comprising a mixture of these components, in accordance with a first embodiment of the invention.

In the process 10, a feed stream 12 comprising a mixture of hexafluoropropylene and hexafluoropropylene oxide (which is typically a product stream emanating from the epoxidation or oxidation of hexafluoropropylene (HFP)), and a stripping agent feed stream 16, comprising fresh and recycled carbon dioxide stripping agent, are fed to an initial or primary stripping packed stripping stage or column 14. In the stripping column 14, the carbon dioxide is contacted with the mixture of hexafluoropropylene and hexafluoropropylene oxide in a counter-current fashion, with the carbon dioxide thereby stripping hexafluoropropylene from the mixture.

Stripped hexafluoropropylene and carbon dioxide (and some entrained hexafluoropropylene oxide) are withdrawn from the stripping stage 14 as a gaseous product 18, while hexafluoropropylene oxide and some absorbed carbon dioxide are withdrawn from the stripping stage 14 as a liquid product 20.

The gaseous product 18 is fed to a first or primary gaseous product distillation stage 22 in which carbon dioxide stripping agent, and hexafluoropropylene and hexafluoropropylene oxide, are recovered from the gaseous product. The carbon dioxide stripping agent is recovered and withdrawn as a distillate 24, while hexafluoropropylene and entrained hexafluoropropylene oxide are recovered and withdrawn as a bottoms product 26. The carbon dioxide distillate 24 is split into a carbon dioxide recycle stream 28 and a carbon dioxide supply stream 30.

The bottoms product 26 is fed to a second stripping stage or column 32, i.e. to a secondary stripping column, in which it is again contacted with stripping agent in the form of carbon dioxide supplied by the carbon dioxide supply stream 30. As with the initial stripping stage, a second gaseous product 34, comprising stripped hexafluoropropylene, and a second liquid product 36, comprising hexafluoropropylene oxide and absorbed carbon dioxide, are withdrawn from the second stripping stage 32.

The second gaseous product 34 is fed to a second gaseous product distillation stage 38, i.e. a secondary distillation stage, in which carbon dioxide is recovered and withdrawn as a distillate 40 and pure hexafluoropropylene (purity >99 mol %) is recovered as a bottoms product 42. The carbon dioxide distillate 34 is combined with the carbon dioxide recycle stream 28 which was recovered in the first gaseous product distillation stage 22, thereby to form recycle stream 50.

The liquid product 36 from the second stripping stage 32 is combined with the liquid product 20 from the first stripping stage and is fed to a third distillation stage 44, i.e. another secondary distillation stage, in which absorbed carbon dioxide is recovered as a distillate 46 and 99.86% pure hexafluoropropylene oxide (purity >99 mol %) is recovered as a bottoms product 48.

The carbon dioxide distillate 46 of the third distillation stage 44 is combined with the recycle stream 50 to form a recycle stream 58. Recycle stream 58 is split into a purge stream 52, which purges carbon dioxide from the process, and a supply stream 54, which is combined with fresh carbon dioxide feed 56 to form the carbon dioxide feed stream 16.

Figure 2:
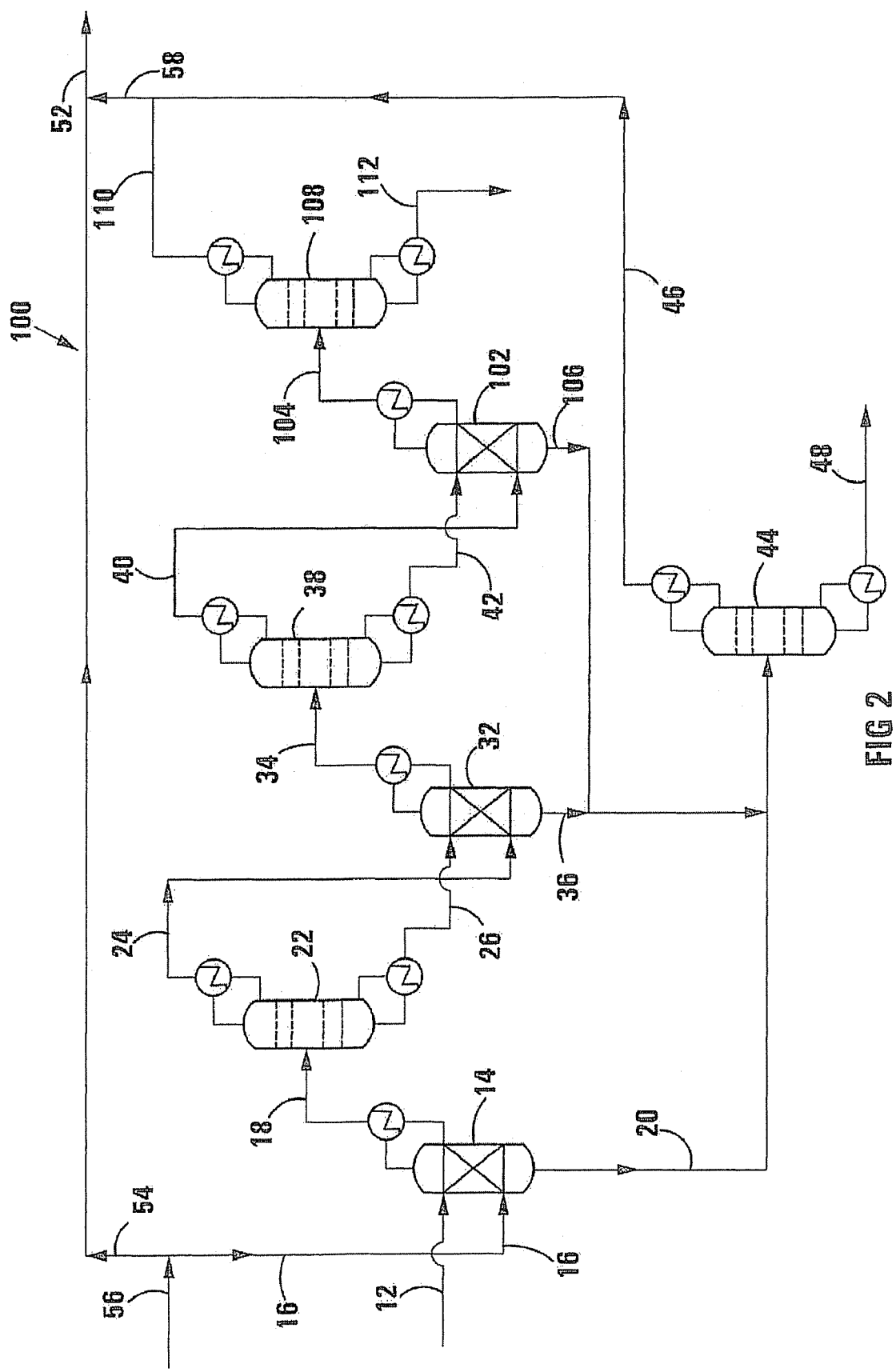
FIG. 2 shows a flow diagram of a process in accordance with a second embodiment of the invention, in which hexafluoroethane is employed as a stripping agent.

Referring now to FIG. 2, reference numeral 100 generally indicates a process for recovering hexafluoropropylene and hexafluoropropylene oxide from a feed stream comprising a mixture of these components, in accordance with a second embodiment of the invention.

The process 100 employs hexafluoroethane (available commercially in South Africa under the designation R116), rather than carbon dioxide, as stripping agent or solvent.

In the process 100, the feed (product) stream 12, comprising a mixture of hexafluoropropylene and hexafluoropropylene oxide, and the stripping agent feed stream 16, comprising fresh and recycled hexafluoroethane as stripping agent, are fed to the initial or primary stripping stage or column 14. In the stripping column 14, the hexafluoroethane is contacted with the mixture of hexafluoropropylene and hexafluoropropylene oxide in a counter-current fashion, the hexafluoroethane thereby stripping hexafluoropropylene from the mixture.

Stripped hexafluoropropylene containing entrained hexafluoropropylene oxide is withdrawn from the stripping stage 14 as gaseous product 18 (which also contains hexafluoroethane) and hexafluoropropylene oxide containing absorbed hexafluoroethane is withdrawn from the stripping stage 14 as the liquid product 20.

The gaseous product 18 is again fed to the first or primary gaseous product distillation stage 22 in which hexafluoroethane stripping agent, and hexafluoropropylene and hexafluoropropylene oxide, are recovered from the gaseous product. The hexafluoroethane stripping agent is recovered and withdrawn as the distillate 24, while hexafluoropropylene and entrained hexafluoropropylene oxide are recovered and withdrawn as the bottoms product 26.

The bottoms product 26 is again fed to the second stripping stage or column 32 in which it is contacted with stripping agent in the form of hexafluoroethane supplied by the hexafluoroethane distillate 24 recovered in the first distillation stage 22. As with the initial stripping stage 14, the second gaseous product 34, comprising stripped hexafluoropropylene and hexafluoroethane, and a second liquid product 36, comprising hexafluoropropylene oxide and absorbed hexafluoroethane, are withdrawn from the second stripping stage 32.

The second gaseous product 34 is, as before, fed to the second gaseous product distillation stage 38 in which hexafluoroethane is recovered and withdrawn as a distillate 40, and hexafluoropropylene and hexafluoropropylene oxide are again recovered and withdrawn as the bottoms product 42.

To increase further the recovery of HFPO, the bottoms product 42 is fed to a third stripping stage 102, i.e. another secondary stripping stage, in which it is contacted with stripping agent in the form of hexafluoroethane supplied by the hexafluoroethane distillate 40 recovered in the second distillation stage 38. Similarly to the stripping stages 14, 32, a third gaseous product 104, comprising stripped hexafluoropropylene, and a third liquid product 106, comprising hexafluoropropylene oxide and absorbed hexafluoroethane, are withdrawn from the third stripping stage 102.

The third gaseous product 104 is fed to a third gaseous product distillation stage 108, i.e. to another secondary distillation unit, in which hexafluoroethane is recovered and withdrawn as a distillate 110, while high purity hexafluoropropylene is recovered as a bottoms product 112.

The liquid product 106 from the third stripping stage 102 is combined with the liquid products 20, 36 from the first and second stripping stages 14, 32 respectively, and the combined product is fed to the secondary distillation stage 44 (which is hence a fourth distillation stage) in which absorbed hexafluoroethane is recovered as the distillate 46 and high purity hexafluoropropylene oxide is recovered as the bottoms product 48.

The hexafluoroethane distillate 46 from the fourth distillation stage 44 is combined with hexafluoroethane distillate 110 from the third distillation stage 108 to form the recycle stream 58. Recycle stream 58 is, as before, split into the purge stream 52, which purges hexafluoroethane from the process, and the hexafluoroethane supply stream 54, which is combined with fresh hexafluoroethane feed 56 to form the carbon dioxide feed stream 16.

HFP ($C_3F_6$) and HFPO ($C_3F_6O$) are specialty fluorocarbons which find extensive use in the fluorochemical industry. HFP is important in both industrial and research activities and is used as an intermediate in chemical reactions, as a monomer in fluoropolymers, in etching applications and in the manufacture of HFPO. HFPO has found application in the manufacture of high performance fluoropolymers and elastomers, in the production of high performance lubricating oils and heat resistant fluids, in surfactant applications, in ion exchange membranes, and in the manufacture of rigid polyurethane foams.

As also indicated hereinbefore, HFPO is typically produced from the oxidation or epoxidation of HFP. During this process there is partial conversion or oxidation of the HFP into HFPO, and the resultant product stream thus contains a mixture of the desired HFPO product and unreacted HFP. In order to utilize the higher value HFPO, the resulting mixture of HFP and HFPO must be practically separated to fulfill two primary aims: (1) to produce a high purity HFPO product stream, and (2) to produce a high purity HFP product stream such that it can be recycled and further oxidized into the higher value HFPO.

The separation of a mixture of HFP and HFPO is difficult due to nature and properties of the two components. HFP is a perfluorinated olefin with three carbon, six fluorine and no active hydrogen atoms, with the double bond on the carbon 1 and carbon 2 atoms. HFPO is chemically similar to HFP. In addition to the three carbon and six fluorine atoms, HFPO contains an oxygen atom in an epoxide or oxirane structure which exists on the carbon 1 and carbon 2 atoms. The chemical similarities of the two components results in a similarity of physical properties, in particular, the boiling points. The normal boiling point of HFP is 243.75 K, while the normal boiling point of HFPO is 245.75 K. With a boiling point difference of 2 K, conventional distillation techniques to effect the separation of a mixture of HFP and HFPO are impractical and thus prohibitive due to the large equilibrium stage requirements.

The Applicant is aware that existing methods used for the separation of HFP and HFPO primarily involve extractive distillation. These methods involve the addition of a third liquid component, a solvent, to depress the volatility of HFP and to increase the volatility of HFPO such that the resulting system is separable by distillation.

The Applicant believes that the process of the present invention involving the use of carbon dioxide or hexafluoroethane as gaseous stripping agent or solvent for HFP unexpectedly presents an efficient and viable alternative process for the recovery of hexafluoropropylene and hexafluoropropylene oxide from a mixture containing these components. Both carbon dioxide and hexafluoroethane show a greater preference for removing HFP from a liquid mixture of HFP and HFPO, with relatively small amounts of HFPO being entrained in both solvents.

By simulating the processes 10, 100 using an Aspen Plus simulation package which is available from Aspen Tech of Canal Park, Cambridge, Mass., USA under the designation Engineering Suite Aspen Plus 2004.1', it has been shown that, with the processes 10, 100, a HFPO product of 99.86 mol % purity and an HFP product of 99.28 mol % purity can be obtained from a feed stream comprising 66 mol % HFPO and 33 mol % HFP, when $CO_2$ is used as the stripping agent. When hexafluoroethane is used as the stripping agent, it is believed that, from the same feed stream, a HFPO product of 99.71 mol % purity and an HFP product of 93.45 mol % purity, can be obtained. In each case, product recoveries are in excess of 99%.

What is claimed is:

1. A process for recovering hexafluoropropylene and hexafluoropropylene oxide from a liquid mixture of these components, the process including in a stripping stage, contacting the mixture with a gaseous stripping agent, thereby to strip hexafluoropropylene from the mixture;

withdrawing a gaseous product comprising hexafluoropropylene and gaseous stripping agent from the stripping stage; and withdrawing a liquid product comprising hexafluoropropylene oxide from the stripping stage.

2. The process according to claim 1, wherein the gaseous stripping agent is carbon dioxide.

3. The process according to claim 1, wherein the gaseous stripping agent is hexafluoroethane.

4. The process according to claim 1, wherein the contacting of the mixture with the gaseous stripping agent is carried out in a packed stripping column, with the gaseous product also containing some entrained hexafluoropropylene oxide, and the liquid product containing some absorbed stripping agent.

5. The process according to claim 4, which includes purifying the gaseous product.

6. The process according to claim 5, wherein the purification of the gaseous product includes recovering, as separate components, hexafluoropropylene, stripping agent and entrained hexafluoropropylene oxide from the gaseous product.

7. The process according to claim 5, wherein the purification of the gaseous product includes distilling it in at least one downstream gaseous product distillation stage, with stripping agent being recovered as a distillate, while the hexafluoropropylene and hexafluoropropylene oxide are recovered as a bottoms product.

8. The process according to claim 7 which includes recovering hexafluoropropylene and hexafluoropropylene oxide from the bottoms product of the downstream gaseous product distillation stage by
- in a secondary stripping stage, contacting the bottoms product with a gaseous stripping agent, thereby to strip hexafluoropropylene from the bottoms product;
- withdrawing a secondary gaseous product comprising hexafluoropropylene and gaseous stripping agent from the secondary stripping stage;
- purifying the secondary gaseous product by distilling it in a secondary downstream gaseous product distillation stage; and
- withdrawing a secondary liquid product comprising hexafluoropropylene oxide from the secondary stripping stage.

9. The process according to claim 8, which includes recovering, from the liquid product from the initial stripping stage, hexafluoropropylene oxide in one or more hexafluoropropylene oxide recovery stages.

10. The process according to claim 9, wherein the recovery of the hexafluoropropylene oxide from the liquid product includes distilling the liquid product in a downstream liquid product distillation stage withdrawing a bottoms product comprising hexafluoropropylene oxide from the liquid product distillation stage, and a withdrawing distillate comprising stripping agent from the liquid product distillation stage.

11. The process according to claim 10, which includes a plurality of the secondary stripping stages each comprising a secondary gaseous product distillation stage and a secondary downstream liquid product distillation stage with the bottoms product from the downstream gaseous product distillation stage of an upstream secondary stripping stage passing into the next or downstream stripping stage, the process further including withdrawing a hexafluoropropylene oxide rich liquid product and a hexafluoropropylene and stripping agent rich gaseous product from each secondary stripping stage with the gaseous product passing into the secondary gaseous product distillation stage of that stripping stage and with the liquid product passing into the secondary liquid product distillation stage of that stripping stage.

12. The process according to claim 11, wherein the bottoms products from the respective secondary liquid product distillation stages are combined to form a composite bottoms product stream.

13. The process according to claim 11, which includes recycling stripping agent which has been recovered from at least one of the gaseous product distillation stages and/or from at least one of the liquid product distillation stages to at least one of the stripping stages.

14. The process according to claim 11, which includes purging stripping agent from the process as a stripping agent purge stream.

* * * * *